United States Patent [19]

Hörrmann

[11] Patent Number: 4,613,621

[45] Date of Patent: Sep. 23, 1986

[54] FATTY ALDEHYDES AND ACIDS IN THE TREATMENT OF NEUROLOGICAL AND INFLAMMATORY DISEASES

[76] Inventor: Wilhelm Hörrmann, 8121 Iffeldorf/OBB, Fed. Rep. of Germany

[21] Appl. No.: 470,969

[22] Filed: Mar. 1, 1983

Related U.S. Application Data

[63] Continuation-in-part of Ser. No. 321,187, Sep. 18, 1981, abandoned, which is a continuation-in-part of Ser. No. 127,817, Mar. 6, 1980, abandoned, which is a continuation-in-part of Ser. No. 29,850, Apr. 13, 1979, abandoned, which is a continuation-in-part of Ser. No. 907,343, May 18, 1978, abandoned, which is a continuation-in-part of Ser. No. 787,902, Apr. 15, 1977, abandoned, which is a continuation-in-part of Ser. No. 682,309, May 3, 1976, abandoned, which is a continuation-in-part of Ser. No. 600,375, Jul. 30, 1985, abandoned, which is a continuation-in-part of Ser. No. 450,458, Mar. 12, 1974, abandoned, which is a continuation-in-part of Ser. No. 274,754, Jul. 24, 1972, abandoned, which is a continuation-in-part of Ser. No. 805,934, Feb. 12, 1969, abandoned, which is a continuation-in-part of Ser. No. 634,884, May 1, 1967, abandoned, which is a continuation-in-part of Ser. No. 412,862, Apr. 20, 1964, abandoned, which is a continuation-in-part of Ser. No. 211,827, Jul. 23, 1972, abandoned, which is a continuation-in-part of Ser. No. 824,798, Jul. 3, 1959, abandoned.

[51] Int. Cl.$^4$ ............................................. A61K 31/11
[52] U.S. Cl. ..................................................... 514/693
[58] Field of Search ......................... 424/331; 514/693

*Primary Examiner*—Stanley J. Friedman

[57] ABSTRACT

This application relates to the administering of fatty aldehydes and acids to patients suffering from neurological and inflammatory diseases.

1 Claim, No Drawings

FATTY ALDEHYDES AND ACIDS IN THE TREATMENT OF NEUROLOGICAL AND INFLAMMATORY DISEASES

CONTINUING DATA

This application is a continuation-in-part of Ser. No. 321,187, filed Sept. 18, 1981, which is a continuation-in-part of Ser. No. 127,817, filed Mar. 6, 1980, which is a continuation-in-part of Ser. No. 29,850, filed Apr. 13, 1979, which is a continuation-in-part of Ser. No. 97,343, filed May 18, 1978, which is a continuation-in-part of Ser. No. 787,802, filed Apr. 15, 1977, which is a continuation-in-part of Ser. No. 682,309, filed May 3, 1976, which is a continuation-in-part of Ser. No. 600,375, filed July 30, 1975 which is a continuation-in-part Ser. No. 450,458, filed Mar. 12, 1974 which is a continuation-in-part of Ser. No. 274,754, filed July 24, 1972, which is a continuation-in-part of Ser. No. 805,934, filed Feb. 12, 1969 which is a continuation-in-part of Ser. No. 634,884, filed May 1, 1967 which is a continuation-in-part of Ser. No. 412,862, filed Apr. 20, 1964.

which is a continuation-in-part of Ser. No. 211,827, filed July 23, 1972, which is a continuation-in-part of Ser. No. 824,798, filed July 3, 1959, all are now abandoned.

INTRODUCTION AND LIST OF INDICATIONS

Certain neurological diseases, namely shaking paralysis and schizophrenia, are according to applicants invention caused by different disorders in the bodies own lipid system, namely that of certain fatty aldehydes and acids.

Inflammatory diseases on the other side are doubtless produced by microorganisms. Some microorganisms however like the tubercle bacillus and the spirochete of syphilis needs for their multiplying a certain predisposition of the affected body. That such predisposition may be called forth by malnutrition for example is known to science for a long time. It is however the subject of this invention that also a disorder in the bodies own lipid system, namely that of fatty aldehydes and acids, may form a predisposition and may be a very important factor for the clinical development of tuberculosis and syphilis. This also true for leprosy. The latter disease is however not referred to in this application as being absent in the United States.

On the other side a special inflammatory disease of the skin namely *akne vulgaris* is for other reasons also belonging to this group.

CHEMISTRY

The compounds of the invention are aliphatic unsaturated compounds. They are unbranched. They are fatty acids and aldehydes. Structural formulae for the compounds are set forth below. The geometric isomers are indicated by "cis" and "trans" notation, and the optical isomers are indicated by $\alpha$ and $\beta$ notation.

| Structural Formulas of the substances |
|---|
| (1) $OHC(CH_2)_4CH=CH(CH_2)_4CH_3$ <br> cis |
| (2) $OHC(CH_2)_4CH=CH(CH_2)_4CH_3$ <br> trans |
| (3) $OHC(CH_2)_6CH=CH(CH_2)_6CH_3$ <br> cis |
| (4) $OHC(CH_2)_6CH=(CH_2)_6CH_3$ <br> trans |
| (5) $HOOC(CH_2)_6CH=CH(CH_2)_6CH_3$ <br> cis |
| (6) $HOOC(CH_2)_6CH=CH(CH_2)_6CH_3$ <br> trans |
| (7) $OHC(CH_2)_4CH=CH(CH_2)_4CH=CH(CH_2)_4CH_3$ <br> cis   cis |
| (8) $OHC(CH_2)_4CH=CH(CH_2)_4CH=CH(CH_2)_4CH_3$ <br> trans   cis |
| (9) $OHC(CH_2)_4CH=CH(CH_2)_4CH=CH(CH_2)_4CH_3$ <br> cis   trans |
| (10) $OHC(CH_2)_4CH=CH(CH_2)_4CH=CH(CH_2)_4CH_3$ <br> trans   trans |
| (11) $\begin{array}{l}\text{OH}\\ OHCC(CH_2)_5CH=CH(CH_2)_6CH=CH(CH_2)_6CH_3\\ \text{H}\end{array}$ <br> alpha  cis  cis |
| (12) $\begin{array}{l}\text{OH}\\ OHCC(CH_2)_5CH=CH(CH_2)_6CH=CH(CH_2)_6CH_3\\ \text{H}\end{array}$ <br> alpha  trans  cis |
| (13) $\begin{array}{l}\text{OH}\\ OHCC(CH_2)_5CH=CH(CH_2)_6CH=(CH_2)_6CH_3\\ \text{H}\end{array}$ <br> alpha  cis  trans |
| (14) $\begin{array}{l}\text{OH}\\ OHCC(CH_2)_5CH=CH(CH_2)_6CH=CH(CH_2)_6CH_3\\ \text{H}\end{array}$ <br> alpha  trans  trans |
| (15) $\begin{array}{l}\text{H}\\ OHCC(CH_2)_5CH=CH(CH_2)_6CH=CH(CH_2)_6CH_3\\ \text{OH}\end{array}$ <br> beta  cis  cis |
| (16) $\begin{array}{l}\text{H}\\ OHCC(CH_2)_5CH=CH(CH_2)_6CH=CH(CH_2)_6CH_3\\ \text{OH}\end{array}$ <br> beta  trans  cis |
| (17) $\begin{array}{l}\text{H}\\ OHCC(CH_2)_5CH=CH(CH_2)_6CH=CH(CH_2)_6CH_3\\ \text{OH}\end{array}$ <br> beta  cis  trans |
| (18) $\begin{array}{l}\text{H}\\ OHCC(CH_2)_5CH=CH(CH_2)_6CH=CH(CH_2)_6CH_3\\ \text{OH}\end{array}$ <br> beta  trans  trans |

| | -continued | | |
|---|---|---|---|
| | Structural Formulas of the substances | | |
| (19) | OH<br>HOOCC(CH$_2$)$_5$CH=CH(CH$_2$)$_6$CH=CH(CH$_2$)$_6$CH$_3$<br>H | | |
| | alpha | cis | cis |
| (20) | OH<br>HOOCC(CH$_2$)$_5$CH=CH(CH$_2$)$_6$CH=CH(CH$_2$)$_6$CH$_3$<br>H | | |
| | alpha | cis | trans |
| (21) | OH<br>HOOCC(CH$_2$)$_5$CH=CH(CH$_2$)$_6$CH=CH(CH$_2$)$_6$CH$_3$<br>H | | |
| | alpha | trans | cis |
| (22) | OH<br>HOOCC(CH$_2$)$_5$CH=CH(CH$_2$)$_6$CH=CH(CH$_2$)$_6$CH$_3$<br>H | | |
| | alpha | trans | trans |
| (23) | H<br>HOOCC(CH$_2$)$_5$CH=CH(CH$_2$)$_6$CH=CH(CH$_2$)$_6$CH$_3$<br>OH | | |
| | beta | cis | cis |
| (24) | H<br>HOOCC(CH$_2$)$_5$CH=CH(CH$_2$)$_6$CH=CH(CH$_2$)$_6$CH$_3$<br>OH | | |
| | beta | cis | trans |
| (25) | H<br>HOOCC(CH$_2$)$_5$CH=CH(CH$_2$)$_6$CH=CH(CH$_2$)$_6$CH$_3$<br>OH | | |
| | beta | trans | cis |
| (26) | H<br>HOOCC(CH$_2$)$_5$CH=CH(CH$_2$)$_6$CH=CH(CH$_2$)$_6$CH$_3$<br>OH | | |
| | beta | trans | trans |

DERIVATIVES OF THE ALDEHYDES

Aldehydes occur in 2 different modifications:
1. in enolic form

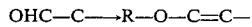

wherein R is H or C
2. in hydrated form

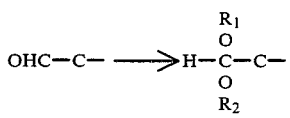

wherein R$_1$ and R$_2$ are identical or different and are H or C.

Typical examples are the ethers of ethanol glycol, glycerol and the esters of acetic acid, opcal/acid and which form noncyclic or cyclic structures

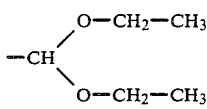 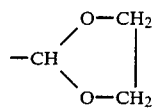

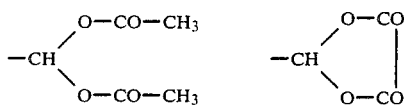

DERIVATIVES OF THE ACIDS

Derivatives of the acids are the salts and the esters. Typical examples are the sodium (Na) salt and the ethanol and glycerol esters.

Important pharmaceutical examples for both fatty aldehydes and fatty acids are the ethers of the aldehydes and the esters of the acids with physiologic acids of bile, namely glyco- and tauro cholic, desoxycholic, lithocholic acids or glycerol.

Physiologic derivatives of fatty aldehydes and acids are the lipids especially those containing glycerol, sphingosin, kolamin, cholin, phosphat, hexoses and the like. Important derivatives of fatty aldehyds (and acids) are the plasmalogens.

How to make the invention:

The synthesis of the claimed fatty aldehydes and acids and their derivatives can be performed in different ways all well known to chemistry and biochemistry. Examples are given in the published U.S. Pat. No. 4,239,756.

How to use the invention:

It is preferred to administer the compounds in form of mixtures containing their isomers in equimolar amounts. For practical reasons the compounds are separated in two groups of isomers:

group I isomers of,
  6-n-docenoic aldehyde
  8-n-hexadecenoic aldehyde
  and 8-n-hexadecenoic acid
group II isomers of
  6,12-n-octadecadienoic aldehyde
  8,16-n-tetracosadienoic-2-hydroxy aldehyde
  and 8,16-n-tetracosadienoic-2-hydroxy acid Group I is indicated in cases of syphilis and tuberculosis, which is augmented by the additional administering of group II too. Though it would be sufficient in syphilis to give only cis or trans isomers of the compounds, it may be more practical for chemical and medical reasons to use all the isomers. In many cases of shaking paralysis (Morbus Parkinson) and in schizophrenia and in *Akne vulgaris* (as in leprosy) it is sufficient to administer only group II of the isomers. Dosage for group I is pro die 50–200 mg/kg of the mixture. The dosage is the same for group II. Dosages are general mean values and may be raised, if necessary. Dosages relate to the free compounds. While parenteral administration should be restricted to emergency cases, the preferred way of administering is the oral one as compounds per se or derivatives combined with glycerol, bile acid, plasmalogen and the like. The compounds may be diluted in plant oils, enclosed in capsules and mixed in emulsions. The total dosage per day must not be given in one single dose but in several doses distributed over the day. Being a substitution therapy the administration must be continued over a long periods of time. In case group I and II of the isomers are administered in combination the dosage is 100–400 mg/kg of the mixture.

I claim:

1. A method of treating tuberculosis in a patient having tuberculosis comprising administering to said patient 100–400 mg/kg daily of at least one of the geometric and optical isomers of 6-n-dodecenoic aldehyde
8-n-hexadecenoic aldehyde and
6,1 2-n-octadecadienoic aldehyde or
8,1 6-n-tetracosadienoic-2-hydroxy aldehyde per se or as an ether of glycol, glycerol or physiologic acids of bile or in form of plasmalogen, said isomer being diluted in plant oils or in the form of capsule or emulsion.

* * * * *